(12) United States Patent
Bharuka et al.

(10) Patent No.: US 9,221,728 B2
(45) Date of Patent: Dec. 29, 2015

(54) METHODS AND APPARATUSES FOR REFORMING OF HYDROCARBONS INCLUDING RECOVERY OF PRODUCTS

(71) Applicant: UOP LLC, Des Plaines, IL (US)

(72) Inventors: Laxmikant Bharuka, Haryana (IN); Sudipta Ghosh, Haryana (IN); Ashutosh Sharma, Haryana (IN); Kenneth David Peters, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 14/639,236

(22) Filed: Mar. 5, 2015

(65) Prior Publication Data

US 2015/0210615 A1    Jul. 30, 2015

Related U.S. Application Data

(62) Division of application No. 13/729,598, filed on Dec. 28, 2012, now Pat. No. 8,999,249.

(51) Int. Cl.
  *C10G 35/24* (2006.01)
  *C07C 7/00* (2006.01)
  *F25J 3/02* (2006.01)

(52) U.S. Cl.
  CPC ............... *C07C 7/005* (2013.01); *C10G 35/24* (2013.01); *F25J 3/0209* (2013.01)

(58) Field of Classification Search
None
See application file for complete search history.

(56) References Cited

U.S. PATENT DOCUMENTS

| | | | | |
|---|---|---|---|---|
| 4,158,026 A | * | 6/1979 | Addison | ............... C07C 15/04 208/66 |
| 4,629,550 A | * | 12/1986 | Dohler | ............... C10G 35/04 208/134 |
| 5,164,070 A | * | 11/1992 | Munro | ............... C10G 49/22 208/100 |
| 8,217,210 B2 | * | 7/2012 | Agrawal | ............... C10B 49/22 48/127.7 |

* cited by examiner

*Primary Examiner* — Tam M Nguyen

(57) ABSTRACT

Embodiments of apparatuses and methods for reforming of hydrocarbons including recovery of products are provided. In one example, a method comprises separating a reforming-zone effluent into a $H_2$, $C_6^-$ hydrocarbon-containing gas phase and a $C_5^+$ hydrocarbon-containing liquid phase. The $H_2$, ($C_1$-$C_{11}$) hydrocarbon-containing gas phase is partially condensed and separated to form a $H_2$, $C_6^-$ hydrocarbon-containing net gas stream and a $C_3^+$ hydrocarbon-containing liquid stream. The $C_5^+$ hydrocarbon-containing liquid phase, the $C_3^+$ hydrocarbon-containing liquid stream, and at least a portion of the $H_2$, $C_6^+$ hydrocarbon-containing net gas stream are introduced to a re-contacting recovery zone for forming a $H_2$-rich stream, a $C_3/C_4$ hydrocarbon-rich LPG stream, and a $C_5^+$ hydrocarbon-rich reformate stream.

20 Claims, 1 Drawing Sheet

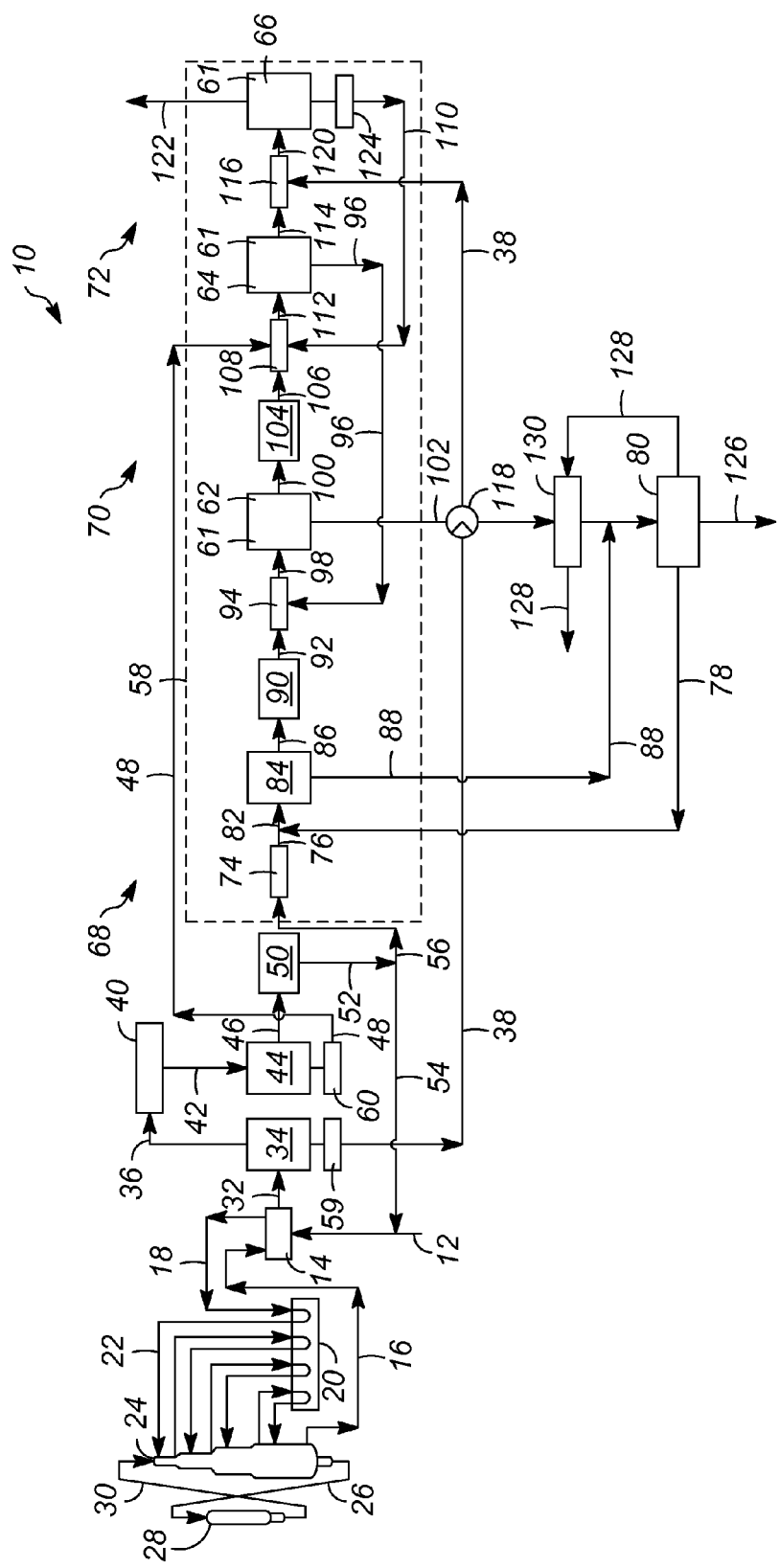

US 9,221,728 B2

METHODS AND APPARATUSES FOR REFORMING OF HYDROCARBONS INCLUDING RECOVERY OF PRODUCTS

CROSS-REFERENCE TO RELATED APPLICATION

This application is a Division of copending application Ser. No. 13/729,598 filed Dec. 28, 2012, now U.S. Pat. No. 8,999,249, the contents of which are hereby incorporated by reference in its entirety.

TECHNICAL FIELD

The technical field relates generally to reforming of hydrocarbons, and more particularly relates to apparatuses and methods for reforming of hydrocarbons with improved recovery of products from a reforming-zone effluent.

BACKGROUND

High octane gasoline is needed for modern gasoline engines. Previously, octane numbers were often improved by incorporating various lead-containing additives into the gasoline. As lead-containing additives have been phased out of gasoline for environmental reasons, it has become increasingly necessary to rearrange the structure of the hydrocarbons used in gasoline blending to achieve higher octane ratings. Catalytic reforming of hydrocarbons is a process widely used by refiners for upgrading the octane ratings of gasoline.

In catalytic reforming, a hydrocarbon feedstock of, for example, $C_5$ hydrocarbons to about $C_{11}$ hydrocarbons, is contacted with a reforming catalyst to convert at least a portion of the heavier hydrocarbons to aromatic hydrocarbons to increase the octane content of gasoline. The catalytic reforming of the heavier hydrocarbons to produce a reformate that includes aromatic hydrocarbons also produces significant quantities of valuable hydrogen and lighter hydrocarbons, such as liquefied petroleum gas (LPG) containing primarily $C_3$ and $C_4$ hydrocarbons. Refiners are looking for ways to maximize the recovery of reforming products, such as reformate, hydrogen and LPG, from the reforming reactor effluent.

Accordingly, it is desirable to provide apparatuses and methods for reforming of hydrocarbons with improved recovery of products from a reforming-zone effluent. Furthermore, other desirable features and characteristics of the present invention will become apparent from the subsequent detailed description and the appended claims, taken in conjunction with the accompanying drawings and this background.

BRIEF SUMMARY

Apparatuses and methods for reforming of hydrocarbons including recovery of products are provided herein. In accordance with an exemplary embodiment, an apparatus for reforming of hydrocarbons including recovery of products comprises a hot separator. The hot separator is configured to receive and separate a reforming-zone effluent (e.g., from combine feed exchanger) that comprises $H_2$, $C_4^-$ hydrocarbons, and $C_5^+$ hydrocarbons including aromatics to form a $H_2$, $(C_1\text{-}C_{11})$ hydrocarbon-containing gas phase and a $C_5^+$ hydrocarbon-containing liquid phase. A product condenser is configured to receive and partially condense the $H_2$, $(C_1\text{-}C_{11})$ hydrocarbon-containing gas phase to form a partially condensed $H_2$, $(C_1\text{-}C_{11})$ hydrocarbon-containing stream. A product separator is configured to receive and separate the partially condensed $H_2$, $(C_1\text{-}C_{11})$ hydrocarbon-containing stream to form a $H_2$, $C_6^-$ hydrocarbon-containing net gas stream and a $C_3^+$ hydrocarbon-containing liquid stream. A re-contacting recovery zone is in fluid communication with the hot separator and the product separator to receive the $C_5^+$ hydrocarbon-containing liquid phase, the $C_3^+$ hydrocarbon-containing liquid stream, and at least a portion of the $H_2$, $C_6^-$ hydrocarbon-containing net gas stream. The re-contacting recovery zone is configured to further separate $H_2$, $C_3/C_4$ hydrocarbons, and/or $C_5^+$ hydrocarbons for forming a $H_2$-rich stream, a $C_3/C_4$ hydrocarbon-rich LPG stream, and a $C_5^+$ hydrocarbon-rich reformate stream.

In accordance with another exemplary embodiment, an apparatus for reforming of hydrocarbons including recovery of products is provided. The apparatus comprises a hot separator configured to receive and separate a reforming-zone effluent that comprises $H_2$, $C_4^-$ hydrocarbons, and $C_5^+$ hydrocarbons including aromatics to form a $H_2$, $C_6^-$ hydrocarbon-containing gas phase and a $C_5^+$ hydrocarbon-containing liquid phase. A product condenser is configured to receive and partially condense the $H_2$, $(C_1\text{-}C_{11})$ hydrocarbon-containing gas phase to form a partially condensed $H_2$, $(C_1\text{-}C_{11})$ hydrocarbon-containing stream. A product separator is configured to receive and separate the partially condensed $H_2$, $(C_1\text{-}C_{11})$ hydrocarbon-containing stream to form a $H_2$, $C_6^-$ hydrocarbon-containing net gas stream and a $C_3^+$ hydrocarbon-containing liquid stream. A re-contacting recovery zone is in fluid communication with the hot separator and the product separator to receive the $C_5^+$ hydrocarbon-containing liquid phase, the $C_3^+$ hydrocarbon-containing liquid stream, and at least a portion of the $H_2$, $C_6^-$ hydrocarbon-containing net gas stream. The re-contacting recovery zone is configured to further separate $H_2$, $C_3/C_4$ hydrocarbons, and/or $C_5^+$ hydrocarbons to form a $H_2$-rich stream and at least one liquid phase stream that comprises $C_3^+$ hydrocarbons. A stabilizer is in fluid communication with the re-contacting recovery zone to receive and separate the at least one liquid phase stream to form a $C_3/C_4$ hydrocarbon-rich LPG stream and a $C_5^+$ hydrocarbon-rich reformate stream.

In accordance with another exemplary embodiment, a method for reforming of hydrocarbons including recovery of products is provided. The method comprises the steps separating a reforming-zone effluent that comprises $H_2$, $C_4^-$ hydrocarbons, and $C_5^+$ hydrocarbons including aromatics into a $H_2$, $(C_1\text{-}C_{11})$ hydrocarbon-containing gas phase and a $C_5^+$ hydrocarbon-containing liquid phase. The $H_2$, $(C_1\text{-}C_{11})$ hydrocarbon-containing gas phase is partially condensed and separated to form a $H_2$, $C_6^-$ hydrocarbon-containing net gas stream and a $C_3^+$ hydrocarbon-containing liquid stream. The $C_5^+$ hydrocarbon-containing liquid phase, the $C_3^+$ hydrocarbon-containing liquid stream, and at least a portion of the $H_2$, $C_6^-$ hydrocarbon-containing net gas stream are introduced to a re-contacting recovery zone for further separation of $H_2$, $C_3/C_4$ hydrocarbons, and/or $C_5^+$ hydrocarbons for forming a $H_2$-rich stream, a $C_3/C_4$ hydrocarbon-rich LPG stream, and a $C_5^+$ hydrocarbon-rich reformate stream.

BRIEF DESCRIPTION OF THE DRAWINGS

The various embodiments will hereinafter be described in conjunction with the following drawing figures, wherein like numerals denote like elements, and wherein:

FIG. 1 schematically illustrates an apparatus and method for reforming of hydrocarbons including recovery of products in accordance with an exemplary embodiment.

DETAILED DESCRIPTION

The following Detailed Description is merely exemplary in nature and is not intended to limit the various embodiments or the application and uses thereof. Furthermore, there is no intention to be bound by any theory presented in the preceding background or the following detailed description.

Various embodiments contemplated herein relate to apparatuses and methods for reforming of hydrocarbons with improved recovery of products from a reforming-zone effluent. The exemplary embodiments taught herein provide a hot separator in fluid communication with a reforming reactor to receive a reforming-zone effluent. The reforming-zone effluent comprises hydrogen ($H_2$), $C_4^-$ hydrocarbons, and $C_5^+$ hydrocarbons including aromatics. As used herein, $C_x$ means hydrocarbon molecules that have "X" number of carbon atoms, $C_x^+$ means hydrocarbon molecules that have "X" and/or more than "X" number of carbon atoms, and $C_x^-$ means hydrocarbon molecules that have "X" and/or less than "X" number of carbon atoms.

In an exemplary embodiment, the reforming-zone effluent is removed from the combined feed exchanger downstream of the reforming reactor as a two phase liquid-gas stream at a relatively high temperature, such as about 80° C. or greater. The hot separator separates the reforming-zone effluent at the relatively high temperature to form a $H_2$, ($C_1$-$C_{11}$) hydrocarbon-containing gas phase and a $C_5^+$ hydrocarbon-containing liquid phase. Separation at the relatively high temperature advantageously forms the $C_5^+$ hydrocarbon-containing liquid phase containing primarily heavier hydrocarbons, such as $C_5$ and $C_6^+$ hydrocarbons. A product condenser is downstream from the hot separator to receive and partially condense the $H_2$, ($C_1$-$C_{11}$) hydrocarbon-containing gas phase to form a partially condensed $H_2$, ($C_1$-$C_{11}$) hydrocarbon-containing stream. A product separator receives and separates the partially condensed $H_2$, ($C_1$-$C_{11}$) hydrocarbon-containing stream to form a $H_2$, $C_6^-$ hydrocarbon-containing net gas stream and a $C_3^+$ hydrocarbon-containing liquid stream.

A re-contacting recovery zone is in fluid communication with the hot separator and the product separator to receive the $C_5^+$ hydrocarbon-containing liquid phase, the $C_3^+$ hydrocarbon-containing liquid stream, and at least a portion of the $H_2$, $C_6^-$ hydrocarbon-containing net gas stream. In an exemplary embodiment, the re-contacting recovery zone is configured as a countercurrent gas and liquid phase re-contacting zone in which the $H_2$, $C_6^-$ hydrocarbon-containing net gas stream is introduced to an initial stage (e.g., upstream section) of the re-contacting recovery zone, the $C_5^+$ hydrocarbon-containing liquid phase is introduced to an end stage (e.g., downstream section) of the re-contacting recovery zone, and the $C_3^+$ hydrocarbon-containing liquid stream is introduced to an intermediate stage of the re-contacting recovery zone between the initial and end stages. As such, gas phase fractions of the $H_2$, $C_6^-$ hydrocarbon-containing net gas stream are advanced downstream countercurrent to and re-contacting with liquid phase fractions of the $C_5^+$ hydrocarbon-containing liquid phase and the $C_3^+$ hydrocarbon-containing liquid stream to further separate $H_2$, $C_3/C_4$ hydrocarbons, and/or $C_5^+$ hydrocarbons. In particular, it has been found that the heavier hydrocarbons contained in the $C_5^+$ hydrocarbon-containing liquid phase facilitate removing the heavier hydrocarbons from the $H_2$, $C_6^-$ hydrocarbon-containing net gas stream for recovering a richer $H_2$-containing stream, e.g., a $H_2$-rich stream, a richer $C_3/C_4$ hydrocarbon-containing stream, e.g., a $C_3/C_4$ hydrocarbon-rich LPG stream, and a richer $C_5^+$ hydrocarbon-containing stream, e.g., a $C_5^+$ hydrocarbon-rich reformate stream.

In an exemplary embodiment, the re-contacting recovery zone forms the $H_2$-rich stream and at least one liquid phase stream that comprises $C_3^+$ hydrocarbons including $C_3/C_4$ hydrocarbons and $C_5^+$ hydrocarbons. A stabilizer is in fluid communication with the re-contacting recovery zone to receive and separate the at least one liquid phase stream to form the $C_3/C_4$ hydrocarbon-rich LPG stream and the $C_5^+$ hydrocarbon-rich reformate stream and the $H_2$ and $C_4^-$ hydrocarbon gas stream.

Referring to FIG. 1, an apparatus 10 for reforming of hydrocarbons in accordance with an exemplary embodiment is provided. A reforming-zone feedstock 12 containing from $C_5$ to about $C_{11}$ hydrocarbons with a boiling point range of, for example, from about 70 to about 205° C. is introduced to a combined feed exchanger 14. The combined feed exchanger 14 operates to exchange heat between a reforming-zone effluent 16 and the reforming-zone feedstock 12. A heated reforming-zone feed stream 18 is withdrawn from the combined feed exchanger 14 and is passed through a heater 20, which is capable of interstage heating of multiple streams, to form a fully heated reforming-zone feed stream 22. The fully heated reforming-zone feed stream 22 is passed to a first stage of a reforming reactor 24 that contains a reforming catalyst as is well known in the art. As illustrated, the reforming reactor 24 is configured for continuous catalyst regeneration where spent catalyst is continuously removed from the reforming reactor 24 via line 26 and passed to a regeneration zone 28 for regeneration. Regenerated catalyst from the regeneration zone 28 is introduced into the reforming reactor 24 via line 30.

At each stage of the reforming reactor 24, a reaction mixture is conducted from the reforming reactor 21 to the heater 20 and then the heated reaction mixture is returned to the reforming reactor 24. A reforming-zone effluent 16 is formed in the reforming reactor 24 and contains $H_2$, a product comprising $C_5^+$ hydrocarbons including aromatics, and lighter hydrocarbons $C_4^-$ hydrocarbons including $C_3$ and $C_4$ hydrocarbons. The reforming-zone effluent 16 is passed along to the combined feed exchanger 11 where heat from the reforming-zone effluent 16 is exchanged with the reforming-zone feedstock 12 to form a partially cooled reforming-zone effluent 32. In an exemplary embodiment, the partially cooled reforming-zone effluent 32 is a two phase liquid-gas stream that is still relatively hot in which hydrogen and the lighter hydrocarbons are predominately in the gas phase and the heavier hydrocarbons are predominately in the liquid phase. In one embodiment, the partially cooled reforming-zone effluent 32 has a temperature of at least about 80° C., such as from about 80 to about 150° C.

The partially cooled reforming-zone effluent 32 is introduced to a hot separator 34. The hot separator 34 separates the partially cooled reforming-zone effluent 32 into a $H_2$, ($C_1$-$C_{11}$) hydrocarbon-containing gas phase 36 and a $C_5^+$ hydrocarbon-containing liquid phase 38. In an exemplary embodiment, the $H_2$, ($C_1$-$C_{11}$) hydrocarbon-containing gas phase 36 has a temperature of from about 80 to about 150° C.

The $H_2$, ($C_1$-$C_{11}$) hydrocarbon-containing gas phase 36 is removed from the hot separator 34 and is passed along to a product condenser 40. The product condenser 40 cools and partially condenses the $H_2$, ($C_1$-$C_{11}$) hydrocarbon-containing gas phase 36 to form a partially condensed $H_2$, ($C_1$-$C_{11}$) hydrocarbon-containing stream 42. As such, some of the heavier hydrocarbons $C_3^+$ hydrocarbons condense into a condensed-liquid phase portion of the partially condensed $H_2$, ($C_1$-$C_{11}$) hydrocarbon-containing stream 42 while $H_2$ and the lighter end hydrocarbons $H_2$ and $C_2^-$ hydrocarbons remain predominantly in the gas phase portion of the partially condensed $H_2$, ($C_1$-$C_{11}$) hydrocarbon-containing stream 42. In an exemplary embodiment, the product condenser 40 forms the partially condensed $H_2$, ($C_1$-$C_{11}$) hydrocarbon-containing stream 42 having a temperature of from about 30 to about 60° C.

The partially condensed $H_2$, ($C_1$-$C_{11}$) hydrocarbon-containing stream 42 is passed along and introduced to a product separator 44. The product separator 44 separates the partially condensed $H_2$, ($C_1$-$C_{11}$) hydrocarbon-containing stream 42 to form a $H_2$, $C_6^-$ hydrocarbon-containing net gas stream 46 from the gas phase portion and a $C_3^+$ hydrocarbon-containing liquid stream 48 from the condensed-liquid portion. In an exemplary embodiment, conditions for operating the product separator 44 include a temperature of from about 30 to about 60° C.

The $H_2$, $C_6^-$ hydrocarbon-containing net gas stream 46 is passed along to a recycle compressor 50 to form a compressed $H_2$, $C_6^-$ hydrocarbon-containing net gas stream 52. In an exemplary embodiment, the recycle compressor 50 compresses the $H_2$, $C_6^-$ hydrocarbon-containing net gas stream 46 to form the compressed $H_2$, $C_6^-$ hydrocarbon-containing net gas stream 52 having a pressure of from about 200 to about 800 kPa gauge. As illustrated, a portion 54 of the compressed $H_2$, $C_6^-$ hydrocarbon-containing net gas stream 52 is combined with the reforming-zone feedstock for introduction to the combined feed exchanger 14.

A portion 56 of the compressed $H_2$, $C_6^-$ hydrocarbon-containing net gas stream 52 is passed along to a re-contacting recovery zone 58. Also and as illustrated, the $C_5^+$ hydrocarbon-containing liquid phase 38 and the $C_3^+$ hydrocarbon-containing liquid stream 48 are passed correspondingly through pumps 59 and 60 and introduced to the re-contacting recovery zone 58. As discussed above, the re-contacting recovery zone 58 may be configured as a countercurrent gas and liquid phase re-contacting zone for further separating $H_2$, $C_3$/$C_4$ hydrocarbons, and/or $C_5^+$ hydrocarbons via extraction and/or absorption by contacting the liquid and gas phase fractions of the $C_5^+$ hydrocarbon-containing liquid phase 38, the $C_3^+$ hydrocarbon-containing liquid stream 48, and at least a portion of the $H_2$, $C_6^-$ hydrocarbon-containing net gas stream 46. Alternatively, the re-contacting recovery zone 58 is not limited to countercurrent flow and that other modes, such as co-current modes as are known in the art, may be used for the re-contacting recovery zone 58.

In an exemplary embodiment, the re-contacting recovery zone 58 comprises a plurality of re-contact drums 61 that are in fluid communication with each other and that include an initial stage re-contact drum 62, an intermediate stage re-contact drum 64 that is downstream from the initial stage re-contact drum 62, and an end stage re-contact drum 66 that is downstream from the intermediate stage re-contact drum 64. While the re-contacting recovery zone 58 is illustrated as having only 3 re-contact drums 61, it is to be understood that the re-contacting recovery zone 58 can have more than 3 re-contact drums 61, such as, for example, one or more additional re-contact drums (with associated equipment items such as a compressor and/or a cooler/chiller as will be discussed in further detail below) may be positioned downstream from the intermediate stage re-contact drum 64 but upstream from the end stage re-contact drum 66.

In an exemplary embodiment, the portion 56 of the compressed $H_2$, $C_6^-$ hydrocarbon-containing net gas stream 52 is introduced to an initial stage section 68 of the re-contacting recovery zone 58, the $C_3^+$ hydrocarbon-containing liquid stream 48 is introduced to an intermediate stage section 70 of the re-contacting recovery zone 58 downstream from the initial stage section 68, and the $C_5^+$ hydrocarbon-containing liquid phase 38 is introduced to an end stage section 72 of the re-contacting recovery zone 58 downstream from the intermediate stage section 70. In particular and as illustrated, the portion 56 of the compressed $H_2$, $C_6^-$ hydrocarbon-containing net gas stream 52 is passed through a product cooler 74 to form a partially condensed, compressed $H_2$, $C_6^-$ hydrocarbon-containing net gas stream 76. In an exemplary embodiment, the product cooler 74 forms the partially condensed, compressed $H_2$, $C_6^-$ hydrocarbon-containing net gas stream 76 having a temperature of from about 30 to about 60° C. A light ends stabilizer stream 78 comprising $H_2$ and $C_2^-$ hydrocarbons is passed along from a stabilizer 80 as will be discussed in further detail below and is combined with the partially condensed, compressed $H_2$, $C_6^-$ hydrocarbon-containing net gas stream 76 to form a combined stream 82. The combined stream 82 is introduced to an initial stage suction drum 84 and is separated to form a suction drum gas phase stream 86 that comprises $H_2$ and $C_6^-$ hydrocarbons and a suction drum liquid phase stream 88 that comprises hydrocarbons.

The suction drum gas phase stream 86 is removed from the initial stage suction drum 84 and is passed along to an initial stage compressor 90. The initial stage compressor 90 compresses the suction drum gas phase stream 86 to form an initial stage compressed gas phase stream 92. In an exemplary embodiment, the initial stage compressed gas phase stream 92 has a pressure of from about 900 to about 1500 kPa gauge and a temperature of from about 90 to about 135° C.

The initial stage compressed gas phase stream 92 is introduced to an initial stage cooler 94 and is combined with an intermediate stage liquid phase stream 96 from the intermediate stage re-contact drum 64 as will be discussed in further detail below. The intermediate stage liquid phase stream 96 comprises $C_3^+$ hydrocarbons. In the initial stage cooler 94, the intermediate stage liquid phase stream 96 and the initial stage compressed gas phase stream 92 are in contact with each other so that similar hydrocarbons, which have an affinity towards each other, can coalesce in a corresponding liquid or gas phase to enrich the respective phase with similar hydrocarbons. As such, a portion of the $C_3^+$ hydrocarbons that may be present in the initial stage compressed gas phase stream 92 are absorbed and/or extracted into the intermediate stage liquid phase stream 96 and some of the $C_2^-$ hydrocarbons that may be present in the intermediate stage liquid phase stream 96 are absorbed and/or extracted into the initial stage compressed gas phase stream 92. Additionally, the initial stage cooler 94 cools the initial stage compressed gas phase stream 92 and the intermediate stage liquid phase stream 96 to facilitate separating $H_2$, $C_3^+$ hydrocarbons and to form an initial stage combined stream 98. In an exemplary embodiment, the initial stage combined stream 98 is a two phase liquid-gas stream that has a temperature of from about 30 to about 60° C.

The initial stage combined stream 98 is removed from the initial stage cooler 94 and is passed along to the initial stage re-contact drum 62. The initial stage combined stream 98 is separated in the initial stage re-contact drum 62 into its two enriched phases to form an initial stage gas phase stream 100 that comprises $H_2$ and $C_6^-$ hydrocarbons and an initial stage liquid phase stream 102 that comprises primarily $C_3$/$C_4$ hydrocarbons and $C_5^+$ hydrocarbons including aromatics.

The initial stage gas phase stream 100 is removed from the initial stage re-contact drum 62 and is passed along to an intermediate stage compressor 104. The intermediate stage compressor 104 compresses the initial stage gas phase stream 100 to form an intermediate stage compressed gas phase stream 106. In an exemplary embodiment, the intermediate stage compressed gas phase stream 106 has a pressure of from about 1200 to about 4000 kPa gauge and a temperature of from about 90 to about 135° C.

The intermediate stage compressed gas phase stream 106 is introduced to an intermediate stage cooler/chiller 108 and is combined with the $C_3^+$ hydrocarbon-containing liquid stream 48 and an end stage liquid phase stream 110 from the end stage re-contact drum 66 as will be discussed in further detail below. The end stage liquid phase stream 110 comprises $C_3^+$ hydrocarbons. In the intermediate stage cooler/chiller 108, the $C_3^+$ hydrocarbon-containing liquid stream 48, the end stage liquid phase stream 110, and the intermediate stage compressed gas phase stream 106 are in contact with each other so that similar hydrocarbons, which have an affinity towards each other, can coalesce in a corresponding liquid or gas phase to enrich the respective phase with similar hydrocarbons. Additionally, the intermediate stage cooler/chiller 108 cools the $C_3^+$ hydrocarbon-containing liquid stream 48, the end stage liquid phase stream 110, and the intermediate stage compressed gas phase stream 106 to facilitate separating $H_2$, $C_3^+$ hydrocarbons and to form an intermediate stage combined stream 112. In an exemplary embodiment, the intermediate stage combined stream 112 is a two phase liquid-gas stream that has a temperature of from about −23 to about 40° C.

The intermediate stage combined stream 112 is removed from the intermediate stage cooler/chiller 108 and is passed along to the intermediate stage re-contact drum 64. The intermediate stage combined stream 112 is separated in the intermediate stage re-contact drum 64 into its two enriched phases to form an intermediate stage gas phase stream 114 that comprises $H_2$ and $C_6^-$ hydrocarbons and the intermediate stage liquid phase stream 96 that comprises $C_3^+$ hydrocarbons, such as $C_3/C_4$ hydrocarbons and $C_5^+$ hydrocarbons including aromatics.

The intermediate stage gas phase stream 114 is removed from the intermediate stage re-contact drum 64 and is passed along to an end stage cooler/chiller 116 and combined with the $C_5^+$ hydrocarbon-containing liquid phase 38. Optionally and as illustrated, the $C_5^+$ hydrocarbon-containing liquid phase 38 may be passed through a heat exchanger 118 for indirect heat exchange with the initial stage liquid phase stream 102 to partially cool the $C_5^+$ hydrocarbon-containing liquid phase 38 upstream from the end stage cooler/chiller 116. In an exemplary embodiment, the $C_5^+$ hydrocarbon-containing liquid phase 38 is partially cooled by the heat exchanger 118 from a temperature of from about 90 to about 150° C. to a temperature of about 60 to about 110° C., and the initial stage liquid phase stream 102 is partially heated by the heat exchanger 118 from a temperature of from about 30 to about 60° C. to a temperature of from about 60 to about 110° C.

In the end stage cooler/chiller 116, the intermediate stage gas phase stream 114 and the $C_5^+$ hydrocarbon-containing liquid phase 38 are in contact with each other so that similar hydrocarbons, which have an affinity towards each other can coalesce in a corresponding liquid or gas phase to enrich the respective phase with similar hydrocarbons. Additionally, the end stage cooler/chiller 116 cools the intermediate stage gas phase stream 114 and the $C_5^+$ hydrocarbon-containing liquid phase 38 to facilitate separating $H_2$, $C_3^+$ hydrocarbons and to form an end stage combined stream 120. In an exemplary embodiment, the end stage combined stream 120 is a two phase liquid-gas stream that has a temperature of from about −23 to about 40° C. In one embodiment, the end stage cooler/chiller 116 is configured as a cooler and the end stage combined stream 120 has a temperature of from about 4 to about 37° C. In another embodiment, the end stage cooler/chiller 116 is configured as a chiller and the end stage combined stream 120 has a temperature of from about −23 to about 40° C.

The end stage combined, stream 120 is removed from the end stage cooler/chiller 116 and is passed along to the end stage re-contact drum 66. The end stage combined stream 120 is separated in the end stage re-contact drum 66 into its two enriched phases to form a $H_2$-rich stream 122 and the end stage liquid phase stream 110. In an exemplary embodiment, the $H_2$-rich stream 122 comprise hydrogen present in an amount of about 90 volume % (vol. %) of the $H_2$-rich stream 122, such as from about 90 to about 96 vol. % of the $H_2$-rich stream 122. The $H_2$-rich stream 122 is removed from the apparatus 10 and may be used, as a product, for example elsewhere in the refinery to help meet hydrogen demands such as for hydroprocessing or the like. As illustrated, the end stage liquid phase stream 110 is passed through a pump 124 and introduced to the intermediate stage cooler/chiller 108 as discussed above.

From the re-contacting recovery zone 58, the suction drum liquid phase stream 88 and the initial stage liquid phase stream 102 are passed along to the stabilizer 80. The stabilizer 80 separates $H_2$ and $C_4^-$ hydrocarbons, $C_3/C_4$ hydrocarbons, and $C_3^+$ hydrocarbons from the suction drum liquid phase stream 88 and, the initial stage liquid phase stream 102 to form the light ends stabilizer stream 78, a $C_3/C_4$ hydrocarbon-rich LPG stream 126, and a $C_5^+$ hydrocarbon-rich reformate stream 128. As illustrated, the $C_5^+$ hydrocarbon-rich reformate stream 128 is passed through a heat exchanger 130 for indirect heat exchange with the initial stage liquid, phase stream 102 and is removed from the apparatus 10 as a reformate product. The $C_3/C_4$ hydrocarbon-rich LPG stream 126 is also removed from the apparatus 10 to be used as an LPG product.

Accordingly, apparatuses and methods for reforming of hydrocarbons with improved recovery of products from a reforming-zone effluent have been described. The exemplary embodiments taught herein provide a hot separator in fluid communication with a reforming reactor to receive a reforming-zone effluent. The hot separator separates the reforming-zone effluent to form a $H_2$, ($C_1$-$C_{11}$) hydrocarbon-containing gas phase and a $C_5^+$ hydrocarbon-containing liquid phase. A product condenser is downstream from the hot separator to receive and partially condense the $H_2$, ($C_1$-$C_{11}$) hydrocarbon-containing gas phase to form a partially condensed $H_2$, ($C_1$-$C_{11}$) hydrocarbon-containing stream. A product separator receives and separates the partially condensed $H_2$, ($C_1$-$C_{11}$) hydrocarbon-containing stream to form a $H_2$, $C_6^-$ hydrocarbon-containing net gas stream and a $C_3^+$ hydrocarbon-containing liquid stream. A re-contacting recovery zone is in fluid communication with the hot separator and the product separator to receive the $C_5^+$ hydrocarbon-containing liquid phase, the $C_3^+$ hydrocarbon-containing liquid stream, and at least a portion of the $H_2$, $C_6^-$ hydrocarbon-containing net gas stream. The re-contacting recovery zone is configured to further separate $H_2$, $C_3/C_4$ hydrocarbons, and/or $C_5^+$ hydrocarbons for forming a $H_2$-rich stream, a $C_3/C_4$ hydrocarbon-rich LPG stream, and a $C_5^+$ hydrocarbon-rich reformate stream.

While at least one exemplary embodiment has been presented in the foregoing detailed description of the disclosure, it should be appreciated that a vast number of variations exist. It should also be appreciated that the exemplary embodiment or exemplary embodiments are only examples, and are not intended to limit the scope, applicability, or configuration of the disclosure in any way. Rather, the foregoing detailed description will provide those skilled in the art with a convenient road map for implementing an exemplary embodiment of the disclosure. It being understood that various changes may be made in the function and arrangement of elements described in an exemplary embodiment without departing from the scope of the disclosure as set forth in the appended claims.

What is claimed is:

1. A method for reforming of hydrocarbons including recovery of products, the method comprising the steps of:
   (a) separating a reforming-zone effluent that comprises $H_2$, $C_4^-$ hydrocarbons, and $C_5^+$ hydrocarbons including aromatics into a $H_2$, ($C_1$-$C_{11}$) hydrocarbon-containing gas phase and a $C_5^+$ hydrocarbon-containing liquid phase;
   (b) partially condensing and separating the $H_2$, ($C_1$-$C_{11}$) hydrocarbon-containing gas phase to form a $H_2$, $C_6^-$ hydrocarbon-containing net gas stream and a $C_3^+$ hydrocarbon-containing liquid stream; and
   (c) introducing the $C_5^+$ hydrocarbon-containing liquid phase, the $C_3^+$ hydrocarbon-containing liquid stream, and at least a portion of the $H_2$, $C_6^-$ hydrocarbon-containing net gas stream to a re-contacting recovery zone for further separation of $H_2$, $C_3$/$C_4$ hydrocarbons, and/or $C_5^+$ hydrocarbons for forming a $H_2$— rich stream, a $C_3$/$C_4$ hydrocarbon-rich LPG stream, and a $C_5^+$ hydrocarbon-rich reformate stream.

2. The method of claim 1 wherein the separating of step (a) is conducted using a hot separator.

3. The method of claim 1 wherein the partial condensing of step (b) is conducted using a product condenser.

4. The method of claim 1 further comprising separating, in a product separator, the partially condensed $H_2$, ($C_1$-$C_{11}$) hydrocarbon-containing stream to form the $H_2$, $C_6^-$ hydrocarbon-containing net gas stream and the hydrocarbon-containing liquid stream and passing the $C_3^+$ hydrocarbon-containing liquid stream to the re-contacting recovery zone.

5. The method of claim 1, wherein the separation of step a is conducted at a temperature of from about 80 to about 150° C.

6. The method of claim 1, wherein the partially condensing of step (b) provides the $H_2$, ($C_1$-$C_{11}$) hydrocarbon-containing stream at a temperature of from about 30 to about 60° C.

7. The method of claim 1, wherein the further separating in the re-contacting recovery zone of step (c) is conducted using a plurality of re-contact drums in fluid communication with each other for separating liquid and/or gas phase fractions of the $C_5^+$ hydrocarbon-containing liquid phase, the $C_3^+$ hydrocarbon-containing liquid stream, and the at least the portion of the $H_2$, $C_6^-$ hydrocarbon-containing net gas stream to further separate $H_2$, $C_3$/$C_4$ hydrocarbons, and/or $C_5^+$ hydrocarbons, the plurality of re-contact drums including an initial stage re-contact drum, an intermediate stage re-contact drum that is downstream from the initial stage re-contact drum, and an end stage re-contact drum that is downstream from the intermediate stage re-contact drum.

8. The method of claim 7, wherein the separating in the re-contacting recovery zone further comprises cooling an intermediate stage gas phase stream that comprises $H_2$ and $C_6^-$ hydrocarbons from the intermediate stage re-contact drum and the $C_5^+$ hydrocarbon-containing liquid phase to form an end stage combined stream using an end stage cooler/chiller that is upstream from the end stage re-contact drum, and introducing and separating the end stage combined stream to the end-stage re-contact drum and form the $H_2$-rich stream and an end stage liquid phase stream that comprises $C_3^+$ hydrocarbons.

9. The method of claim 8, wherein the end stage combined stream has a temperature of from about –23 to about 40° C.

10. The method of claim 8, wherein the separating in the re-contacting recovery zone further comprises:
    compressing an initial stage gas phase stream that comprises $H_2$ and $C_6^-$ hydrocarbons from the initial stage re-contact drum to form an intermediate stage compressed gas phase stream using an intermediate stage compressor that is upstream from an intermediate stage cooler/chiller;
    cooling the intermediate stage compressed gas phase stream, the $C_3^+$ hydrocarbon-containing liquid stream, and the end stage liquid phase stream to form an intermediate stage combined stream using the intermediate stage cooler/chiller; and
    separating the intermediate stage combined stream in an intermediate stage re-contact drum to form the intermediate stage gas phase stream and an intermediate stage liquid phase stream that comprises $C_3^+$ hydrocarbons.

11. The method of claim 10, wherein the intermediate stage compressed gas phase stream has a pressure from about 1200 to about 4000 kPa gauge and a temperature of from about 90 to about 135° C.

12. The method of claim 10, wherein the intermediate stage combined stream has a temperature from about –23 to about 40° C.

13. The method of claim 10, wherein the separating in re-contacting recovery zone further comprises:
    compressing the at least the portion of the $H_2$, $C_6^-$ hydrocarbon-containing net gas stream to form an initial stage compressed gas phase stream using an initial stage compressor that is upstream from the initial stage cooler;
    cooling the initial stage compressed gas phase stream and the intermediate stage liquid phase stream to form an initial stage combined stream using the initial stage cooler that is upstream from an initial stage re-contact drum; and
    separating the initial stage combined stream in the initial stage re-contact drum to form the initial stage gas phase stream and an initial stage liquid phase stream that comprises $C_3^+$ hydrocarbons.

14. The method of claim 13, wherein the initial stage compressed gas phase stream has a pressure from about 800 to about 1600 kPa gauge and a temperature of from about 90 to about 135° C.

15. The method of claim 13, wherein the initial stage combined stream has a temperature from about 30 to about 60° C.

16. The method of claim 13, further comprising:
    heat exchanging, indirectly, the $C_5^+$ hydrocarbon-containing liquid phase and the initial stage liquid phase stream to partially cool the $C_5^+$ hydrocarbon-containing liquid phase upstream from the end stage cooler/chiller.

17. The method of claim 16, further comprising:
    compressing the $H_2$, $C_6^-$ hydrocarbon-containing net gas stream to form a compressed $H_2$, $C_6^-$ hydrocarbon-containing net gas stream using a recycle compressor;
    a product cooler configured to receive and partially condense at least a portion of the compressed $H_2$, $C_6^-$ hydrocarbon-containing net gas stream to form a partially condensed, compressed $H_2$, $C_6^-$ hydrocarbon-containing net gas stream;
    separating the partially condensed, compressed $H_2$, $C_6^-$ hydrocarbon-containing net gas stream to form a suction drum gas phase stream that comprises $H_2$ and $C_6^-$ hydrocarbons and a suction drum liquid phase stream that comprises $C_3^+$ hydrocarbons using an initial stage suction drum; and
    compressing, in the initial stage compressor, the suction drum gas phase stream to form the initial stage compressed gas phase stream.

18. The method of claim 17, further comprising:
    separating the suction drum liquid phase stream and the initial stage liquid phase stream to form the $C_3$/$C_4$ hydrocarbon-rich LPG stream and the $C_5^+$ hydrocarbon-rich reformat, stream using a stabilizer that is in fluid communication with the initial stage suction drum and the initial stage re-contact drum.

19. The method of claim 18, further comprising separating the suction drum liquid phase stream and the initial stage liquid phase stream in the stabilizer to form a light ends stabilizer stream comprising $H_2$ and $C_3^-$ hydrocarbons, and separating the light ends stabilizer stream and the partially condensed, compressed $H_2$, $C_6^-$ hydrocarbon-containing net gas stream in the initial stage suction drum to form the suction drum gas phase and liquid phase streams.

20. A method for reforming of hydrocarbons including recovery of products, the method comprising:

separating a reforming-zone effluent comprising $H_2$, $C_4^-$ hydrocarbons, and $C_5^+$ hydrocarbons including aromatics to form a $H_2$, $(C_1-C_{11})$ hydrocarbon-containing gas phase and a $C_5^+$ hydrocarbon-containing liquid phase;

partially condensing the $H_2$, $(C_1-C_{11})$ hydrocarbon-containing gas phase to form a partially condensed $H_2$, $(C_1-C_{11})^-$ hydrocarbon-containing stream;

separating the partially condensed $H_2$, $(C_1-C_{11})$ hydrocarbon-containing stream to form a $H_2$, $C_6^-$ hydrocarbon-containing net gas stream and a $C_3^+$ hydrocarbon-containing liquid stream;

separating, in a re-contacting recovery zone, the $C_5^+$ hydrocarbon-containing liquid phase, the $C_3^+$ hydrocarbon-containing liquid stream, and at least a portion of the $H_2$, $C_6^-$ hydrocarbon-containing net gas stream to form a $H_2$-rich stream and at least one liquid phase stream that comprises hydrocarbons; and separating, in a stabilizer in fluid communication with the re-contacting recovery zone, the at least one liquid phase stream to form a $C_3/C_4$ hydrocarbon-rich LPG stream and a $C_5^+$ hydrocarbon-rich reformate stream.

* * * * *